(12) United States Patent
Adachi et al.

(10) Patent No.: US 7,914,813 B2
(45) Date of Patent: Mar. 29, 2011

(54) INTERFACE FOR TRANSDERMAL DRUG ADMINISTRATION DEVICE

(75) Inventors: Hirotoshi Adachi, Tsukuba (JP); Seiji Tokumoto, Tsukuba (JP); Naruhito Higo, Tsukuba (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 1274 days.

(21) Appl. No.: 10/588,168

(22) PCT Filed: Feb. 2, 2005

(86) PCT No.: PCT/JP2005/001525
§ 371 (c)(1),
(2), (4) Date: Aug. 2, 2006

(87) PCT Pub. No.: WO2005/075016
PCT Pub. Date: Aug. 18, 2005

(65) Prior Publication Data
US 2007/0123837 A1  May 31, 2007

(30) Foreign Application Priority Data
Feb. 3, 2004  (JP) ................... 2004-026327

(51) Int. Cl.
*A61F 13/00* (2006.01)
(52) U.S. Cl. ........................................ 424/449
(58) Field of Classification Search ........................ None
See application file for complete search history.

(56) References Cited

U.S. PATENT DOCUMENTS
3,964,482 A * 6/1976 Gerstel et al. ............... 604/890.1
2006/0222723 A1* 10/2006 Bevilacqua ................... 424/769

FOREIGN PATENT DOCUMENTS
WO  WO 02/32480 A2  4/2002
WO  WO 02/094368 A1  11/2002

OTHER PUBLICATIONS
JP 2002-079499, Patent Abstracts of Japan & English translation thereof, dated Mar. 19, 2002.
JP 2003-093521, Patent Abstracts of Japan & English translation thereof, dated Apr. 2, 2003.
JP-2000-512529 A (a family member of WO97/348440) dated Dec. 24, 1997).
JP-2001-506904 A (a family member of WO98/28037) dated Jul. 2, 1998.

* cited by examiner

*Primary Examiner* — Michael G Hartley
*Assistant Examiner* — Paul Dickinson
(74) *Attorney, Agent, or Firm* — Townsend & Banta

(57) ABSTRACT

It is intended to provide an interface for a transdermal drug administration device that can supply a drug almost evenly and favorably from a plurality of projections through skin. This interface for a transdermal drug administration device has a flat plate 8. The flat plate 8 comprises a plurality of two-dimensionally arranged conical or pyramidal projections 6 capable of piercing skin and a plurality of openings 7 capable of delivering a drug which are respectively arranged in correspondence with the projections. The openings 7 are respectively arranged in proximity to their corresponding projections 6. The flat plate 8 can be made of a metal or ceramics. The ratio between the number of the openings and the number of the projections can be 1:1 to 1:2.

1 Claim, 2 Drawing Sheets

INTERFACE FOR TRANSDERMAL DRUG ADMINISTRATION DEVICE

TECHNICAL FIELD

The present invention relates to an interface for a transdermal drug administration device intended to administer a drug through the skin. Particularly, the present invention relates to an interface for a transdermal drug administration device comprising projections capable of piercing the skin.

BACKGROUND ART

Methods for administering a drug by attaching a drug-containing adhesive skin patch to the skin and penetrating the drug from this adhesive skin patch into the skin have commonly been performed so far. On the other hand, administration methods using electrical energy such as iontophoresis (Journal of Pharmaceutical Sciences, Vol. 76, p. 341, 1987) and electroporation (National Publication of International Patent Application No. 1991-502416; and Proc. Natl. Acad. Sci. USA, Vol. 90, pp. 10504-10508, 1993) have been developed as methods for promoting the drug absorption of the skin or mucous membrane. Both iontophoresis and electroporation have been expected to be used as methods for promoting transdermal or transmucosal drug absorption.

Alternatively, Patent Document 1 has proposed a device for increasing transdermal flux of a transdermal pharmaceutical agent by mechanically piercing the skin before the release thereof, in relation to the promotion of drug absorption. This device comprises a sheet having a plurality of openings, a plurality of microblades being integral therewith and extending downward therefrom, and means for anchoring the device to a body surface. In the disclosure, it is intended to provide a device produced at high yields and low costs in a reproducible fashion, which is suitable for minimizing inflammation of the skin and improving the attachment thereof to the skin. A similar device thereto has also been proposed in Patent Document 2.

[Patent Document 1]: National Publication of International Patent Application No. 2000-512529
[Patent Document 2]: National Publication of International Patent Application No. 2001-506904

Furthermore, Patent Document 3 has proposed a device comprising a drug administration tool equipped with a large number of needles for drug administration intended to administer a drug through the skin or mucous membrane by an iontophoretic driving. This device has a needle support and a large number of needles for drug administration provided on the side of the needle support contacting the skin or mucous membrane and is constructed so that the tips of the needles for drug administration located in the vicinity of the center of the needle support protrude further than the tips of the needles for drug administration located in the periphery of the needle support. In the disclosure, it is intended to provide a device that can unerringly insert the fine needles of the drug administration tool into a medicated site when administering a drug by an iontophoretic driving, reduce stimulation to the skin by reasonably dispersing an electric current, and easily control a dose.

[Patent Document 3]: Japanese Patent Laid-Open No. 2003-93521

However, the microblades for piercing skin in the devices disclosed in Patent Documents 1 and 2 are formed by bending the sheet having openings at the positions of the openings. This device might fail to perform reliable piercing treatment because the microblades are flat and therefore deflect by the skin. The microblades present a challenge in that they require exceedingly fine and highly sophisticated machining (punching). Moreover, in the device disclosed in Patent Document 3, the whole platelike member in the main body of the needle support has a lattice pattern, wherein drug-guiding paths are formed, and the needle for drug administration is provided at the position of each lattice point. In this device, when the drug-guiding paths are narrowed, a drug that has passed through the drug-guiding paths is difficult to evenly supply to the needles for drug administration arranged around the drug-guiding paths, depending on the degree of uneven roughness of the surface of the platelike member. Moreover, the amount of the drug supplied from each of the needles for drug administration through skin might vary from one needle for drug administration to another.

Thus, an object of the present invention is to provide an interface for a transdermal drug administration device that can supply a drug almost evenly and favorably from a plurality of projections through skin.

DISCLOSURE OF THE INVENTION

The object is attained with an interface for a transdermal drug administration device having a flat plate comprising a plurality of two-dimensionally arranged conical or pyramidal projections capable of piercing the skin and a plurality of openings capable of delivering a drug which are respectively arranged in correspondence with the projections, wherein the openings are respectively arranged in proximity to their corresponding projections.

In this context, channels for directing a drug from the openings to their corresponding projections can be provided between the openings and their corresponding projections on the flat plate. It is preferred that the projections should be, for example 100 to 700 μm in height, that the lower bases of the projections should be, for example 30 to 200 μm in diameter, and that the openings should be, for example 50 to 2000 μm in diameter. It is also preferred that the ratio between the number of the openings and the number of the projections should be 1:1 to 1:2. The flat plate can be made of a metal or ceramics.

According to the present invention, an interface for a transdermal drug administration device that can supply a drug almost evenly and favorably from a plurality of projections through skin can be obtained.

BRIEF DESCRIPTION OF THE DRAWINGS

FIGS. 2(a) and 2(b) are a perspective view and a sectional view taken along the A-B line of FIG. 2a), respectively;

DESCRIPTION OF REFERENCE NUMERALS

Figure 1:
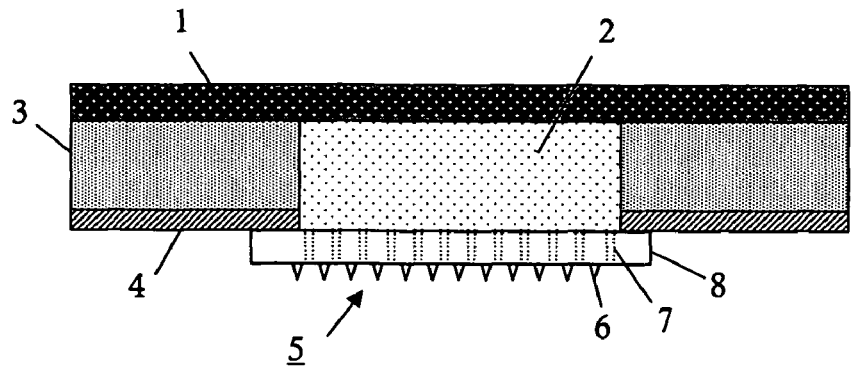
FIG. 1 is a sectional view showing one example of a transdermal drug administration device using an interface for a transdermal drug administration device according to the present invention.

1 support
2 drug-containing layer
3 wall member 4 adhesive layer
5 interface for a transdermal drug administration device
6 projection
7 opening
8 flat plate

BEST MODE FOR CARRYING OUT THE INVENTION

FIG. 1 is a sectional view showing one example of a transdermal drug administration device using an interface for a transdermal drug administration device according to the present invention. The transdermal drug administration device of this example comprises a support 1, a drug-containing layer 2 placed on the support 1, a wall member 3 placed on the support 1 so as to surround the drug-containing layer 2, an adhesive layer 4 provided on the side of the support 1 adhering to skin, and an interface 5 for a transdermal drug administration device provided on the side of the drug-containing layer 2 adhering to skin. The drug-containing layer 2 retains a drug, for example in a liquid form. The interface 5 for a transdermal drug administration device has a flat plate 8 comprising a plurality of conical or pyramidal projections 6 capable of piercing skin and a plurality of openings 7 capable of delivering a drug which are respectively arranged in correspondence with the projections, as shown in the drawing.

The transdermal drug administration device of this example, when used, is affixed to the skin by means of the adhesive layer 3 by putting the interface 5 for a transdermal drug administration device on the skin and pressing the device against the skin from above. As a result, the plurality of projections 6 provided on the interface 5 for a transdermal drug administration device pierce the skin (stratum corneum). A drug in a liquid form is thereby transferred from the drug-containing layer 2 though the plurality of openings 7 provided on the flat plate 8 to the skin side. This transferred drug in a liquid form flows from the roots of the plurality of projections 6 to the tips thereof and penetrates through holes on the skin formed by the projections 6 into the body.

In the transdermal drug administration device of this example, materials described below can be used for each member.

A non-water-permeable material is selected for the support, and examples thereof include polyolefin, polyurethane, polystyrene, rubber, EVA, PVC, and PET.

A non-water-permeable material is selected for the wall member, and examples thereof include foamed polyolefin (e.g., PE and PP), foamed polyurethane, foamed polystyrene, foamed rubber (e.g., polybutylene), foamed EVA, and foamed PVC. For example, foamed polyolefin is preferable.

Examples of a material for the adhesive layer include natural rubber, styrene-isoprene-styrene block copolymers, styrene-butadiene rubber, styrene-isoprene rubber, polyisobutylene, polyisoprene, polyacrylate, and silicone rubber. For example, polyacrylate is preferable.

The drug-containing layer may be made of a material that can retain a drug in a liquid form, and examples thereof include: porous materials such as nonwoven fabrics, woven fabrics, gauze, and sponge made of polyester (polyethylene terephthalate), polysaccharides or cellulose derivatives (rayon or cotton), or polyamide (nylon); hydrophilic polymers such as agar, agarose, alginic acid, xanthan gum, guar gum, dextran, dextrin, pullulan, chitosan, gelatin, carboxyvinyl polymers, polyacrylate, carboxymethyl cellulose salt, polyoxyalkylene, polyvinyl alcohol, polyvinyl pyrrolidone, and polyacrylamide; and ion-exchange resins such as Amberlite, Diaion, and cholestyramine. For example, a nonwoven fabric mainly composed of rayon is preferable.

A variety of drugs appropriate to the purpose of treatment can be selected as the drug. As long as they are, for example, compounds having pharmacological activities, the type of the drug and the type of salt, the adaptation of the drug, and so on, are not particularly limited. Examples of the drug used include antibiotics, antimycotics, antitumor agents, cardiotonics, antiarrhythmic agents, vasodilators, hypotensive agents, diuretics, hypotensive diuretics, agents for circulatory organ, antiplatelet drugs, hemostatics, antilipidemic agents, antipyretic/analgesic/antiphlogistic agents, antirheumatic agents, relaxants, antitussive expectorants, antiulcer agents, sedatives, antiepileptics, antidepressants, antiallergic agents, antidiabetics, antituberculous agents, hormonalagents, narcoticantagonists, osteoclastic inhibitors, angiogenic inhibitors, and local anesthetics.

The interface for a transdermal drug administration device is described later in detail.

The transdermal drug administration device is illustrated here as a usual adhesive skin patch. However, the transdermal drug administration device of the present invention is not limited to this form and can also be used as an iontophoresis or electroporation device that conducts an administration method using electrical energy, by adding an electrode to the device of this example.

Figure 2:
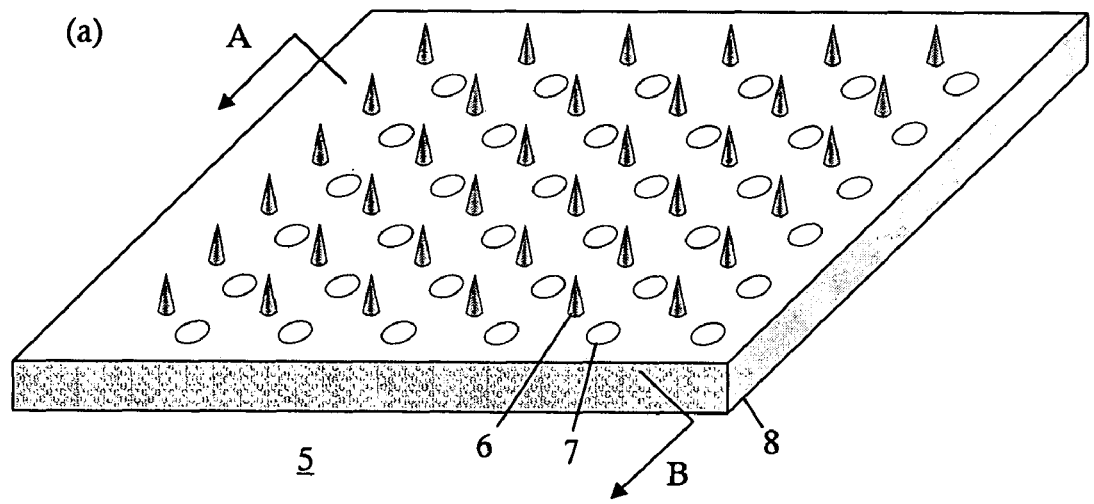
FIG. 2 is a diagram showing one example of the interface for a transdermal drug administration device according to the present invention.
Figure 2:
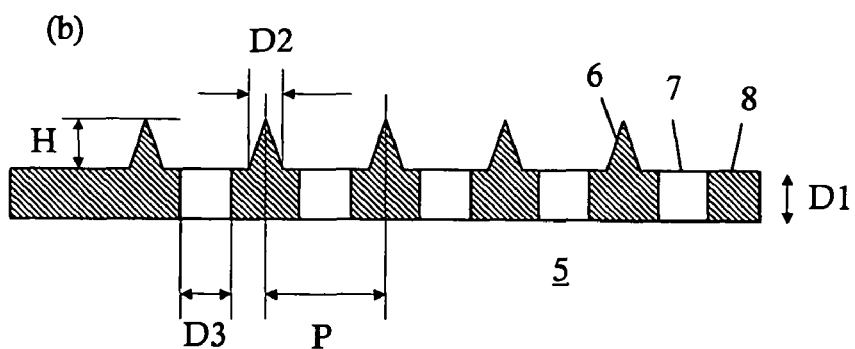
Figure 3:
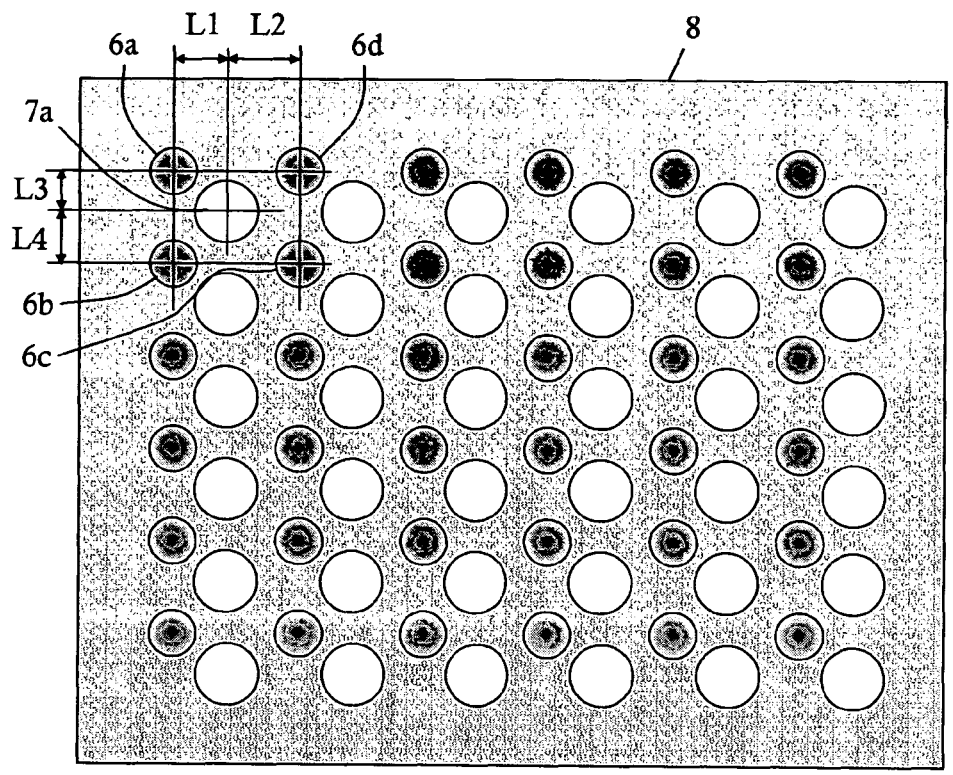
FIG. 3 is a plane view of the interface for a transdermal drug administration device shown in FIG. 2.

FIG. 2 is a diagram showing one example of the interface for a transdermal drug administration device according to the present invention, and FIGS. 2(a) and 2(b) are a perspective view and a sectional view taken along the A-B line of FIG. 2(a), respectively. FIG. 3 is a plane view of the interface for a transdermal drug administration device shown in FIG. 2. As shown in FIGS. 2(a) and 2(b), an interface 5 for a transdermal drug administration device has a flat plate 8. The flat plate 8 comprises a plurality of two-dimensionally arranged conical or pyramidal projections 6 capable of piercing skin and a plurality of openings 7 capable of delivering a drug which are respectively arranged in correspondence with the projections.

In this context, the openings 7 are respectively arranged in proximity to their corresponding projections 6. The phrase "arranged in proximity" means that the distance between a particular projection and its corresponding opening is smaller than the distance between the particular projection and an opening that does not correspond thereto, and as a result, the particular projection and its corresponding opening are arranged close to each other. This arrangement will be described with reference to the example shown in FIG. 3. In FIG. 3, a plurality of projections 6 and a plurality of openings 7 are alternately arranged in a tetragonal lattice. The ratio between the number of the projections 6 and the number of the openings 7 is 1:1. Now taking a close look at four adjacent projections 6a to 6d and an opening 7a surrounded by the projections, straight lines intersecting the centers of each of the projections 6a to 6d and the opening 7a are drawn in the vertical and horizontal directions of the tetragonal lattice. As shown in the drawing, line segments L1 and L2 are obtained in the horizontal direction, while line segments L3 and L4 are obtained in the vertical direction. In FIG. 3, when the opening 7a is arranged in proximity to its corresponding projection 6a, this means that the relationship of L1/L2<1 and L3/L4<1 is satisfied. This relationship is preferably L1/L2<0.9 and L3/L4<0.9, more preferably L1/L2<0.8 and L3/L4<0.8.

When the openings are respectively arranged in proximity to their corresponding projections, a drug easily flows, for example in FIG. 3, through the opening 7a into its corresponding projection 6a. Similarly, a drug easily flows through other openings 7b to 7d into their respective corresponding projections 6b to 6d. The same holds true for the remaining projections and openings. The drug can thereby be supplied almost evenly from each of the projections through skin into the body. The projections are conical or pyramidal in shape and as such, can unerringly pierce skin without deflection even when the transdermal drug administration device is pressed against the skin. The drug can thereby be supplied favorably from each of the projections through skin into the body.

Figure 4:
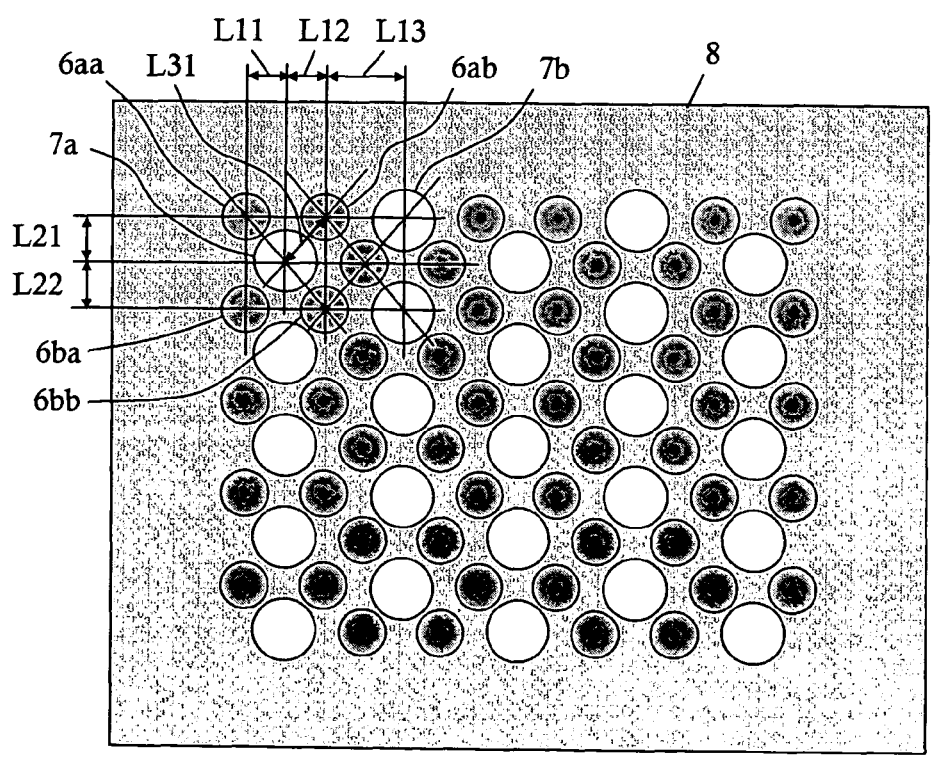
FIG. 4 is a plane view showing another example of the interface for a transdermal drug administration device according to the present invention.

FIG. 4 is a plane view showing another example of the interface for a transdermal drug administration device according to the present invention. In this example, a plurality of projections 6 and a plurality of openings 7 are arranged as shown in the drawing. The ratio between the number of the projections 6 and the number of the openings 7 is 2:1. Now taking a close look at four adjacent projections 6aa, 6ab, 6ba, and 6bb and an opening 7a surrounded by the projections and its adjacent opening 7b, straight lines intersecting the centers of each of the projections 6aa, 6ab, 6ba, and 6bb and the openings 7a and 6b are drawn in the vertical, horizontal, and slanting directions. As shown in the drawing, line segments L11, L12, and L13 are obtained in the horizontal direction, line segments L21 and L22 are obtained in the vertical direction, and a line segment L31 is obtained in the slanting direction. In FIG. 4, when the opening 7a is arranged in proximity to a pair of its corresponding projections 6aa and 6ab, this means that the relationship of L11/L12=1 and L31/L13<1 and L21/L22<1 is satisfied. This relationship is preferably L11/L12=1 and L31/L13<0.9 and L21/L22<0.9, more preferably L11/L12=1 and L31/L13<0.8 and L21/L22<0.8.

In this case as well, a drug easily flows through the opening 7a into a pair of its corresponding projections 6aa and 6ab. Similarly, a drug easily flows through the remaining openings into pairs of their corresponding projections. The drug can thereby be supplied almost evenly from each of the projections through skin into the body. The projections are conical or pyramidal in shape and as such, can unerringly pierce skin without deflection even when the transdermal drug administration device is pressed against the skin. The drug can thereby be supplied favorably from each of the projections through skin into the body.

In the interface for a transdermal drug administration device shown in FIG. 3 or 4, channels (not shown) for directing a drug from the openings 7 to (pairs of) their corresponding projections 6 can be provided between the projections 6 and their corresponding openings 7 on the flat plate 8. A drug flows more easily from the openings into their corresponding projections by virtue of these channels. The drug can thereby be supplied almost evenly from each of the projections through skin into the body.

In the interface for a transdermal drug administration device, materials described below can be used for each member.

Examples of a material that can be used for the flat plate include: metal, alloy, and ceramics such as Ti, Ti alloy, Ag, $SiO_2$, Pt, stainless steel, carbon, and hydroxyapatite; and plastics such as polystyrene, polyester, PMMA, ABS, PP, PE, PLA (polylactic acid), PGA (polyglycolic acid), PLGA (lactic acid-polyglycolic acid copolymer), and HEMA. These materials can be used alone or as composite materials and can appropriately be coated to give electrochemically/dynamically preferable interface properties. A thickness D1 of the flat plate is preferably 0.1 to 3.0 mm.

The projections can be formed by processing the flat plate. For example, etching or die cast molding can be used as a processing method. It is preferred that the projections should be conical or pyramidal in shape and be sharp-pointed. In this context, the phrase "conical or pyramidal" is not limited to conical or pyramidal shapes and is broadly defined to represent all similar shapes including shapes that taper down seamlessly or stepwise in the upward direction from the lower base of the projection. A height H of the projection is preferably 100 to 700 μm. A diameter D2 of the lower base of the projection is preferably 30 to 200 μm. The number of the projections formed on the flat plate is preferably 1000 to 2000 projections/plates. A pitch P between the projections is preferably, for example 200 to 600 μm.

The openings are holes formed by processing the flat plate. For example, etching, die cast molding, or laser processing can be used as a processing method. The shapes of the openings include, but not limited to, circles and polygons. A diameter D3 of the opening is preferably 50 to 2000 μm. The number of the openings formed on the flat plate is preferably 1000 to 2000 openings/plates.

The ratio between the number of the openings and the number of the projections is preferably 1:1 to 1:2.

When the projections are conical in shape, and the area (per unit cell) of the lower base thereof, the area (per unit cell) of the opening, and the area of the unit cell are defined as S1, S2, and S3, respectively, it is preferred that the following relationship should be satisfied for performing favorable drug administration:

$0.5 \times S3 > S1 > 0.005 \times S3$; and $0.40 \times S3 > S2 > 0.04 \times S3$.

In the present invention, such constitution could conduct reliable piercing treatment on skin (stratum corneum) and could favorably penetrate a drug from the drug-containing layer through the openings and the projections on the flat plate into skin (confirmed by the skin staining of a die).

INDUSTRIAL APPLICABILITY

An interface for a transdermal drug administration device according to the present invention is available in medical fields and can supply a drug almost evenly and favorably from a plurality of projections through skin into the body.

The invention claimed is:

1. An interface for a transdermal drug administration device having a flat plate formed from polylactic acid comprising a plurality of two-dimensionally arranged conical or pyramidal projections capable of piercing the skin and a plurality of openings spaced from the conical or pyramidal projections and capable of delivering a drug, said openings being respectively arranged in correspondence with the projections, wherein the distance between a particular projection and its corresponding opening is smaller than the distance between the particular projection and an opening that does not correspond thereto, wherein channels are provided on the surface of the flat plate between the openings and their corresponding projections for directing a drug from the openings to their corresponding projections, said projections being 100 to 700 μm in height, lower bases of the projections being 30 to 200 μm in diameter, said openings being 50 to 2000 μm in diameter, and the ratio between the number of the openings and the number of the projections being 1:1 to 1:2.

* * * * *